US010080624B2

(12) United States Patent
Mickle et al.

(10) Patent No.: US 10,080,624 B2
(45) Date of Patent: Sep. 25, 2018

(54) POWERING AND READING IMPLANTED DEVICES

(71) Applicants: UNIVERSITY OF PITTSBURGH—OF THE COMMONWEALTH SYSTEM OF HIGHER EDUCATION, Pittsburgh, PA (US); Philip E. Levy

(72) Inventors: Marlin H. Mickle; Joshua R. Stachel, Pittsburgh, PA (US); Kara Nicole-Simms Bocan, North Huntingdon, PA (US); Ervin Sejdic, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/889,165

(22) PCT Filed: May 12, 2014

(86) PCT No.: PCT/US2014/037621
§ 371 (c)(1),
(2) Date: Nov. 5, 2015

(87) PCT Pub. No.: WO2014/186245
PCT Pub. Date: Nov. 20, 2014

(65) Prior Publication Data
US 2016/0135917 A1 May 19, 2016

Related U.S. Application Data

(60) Provisional application No. 61/823,598, filed on May 15, 2013.

(51) Int. Cl.
*A61B 90/98* (2016.01)
*A61B 5/00* (2006.01)
(Continued)

(52) U.S. Cl.
CPC .............. *A61B 90/98* (2016.02); *A61B 5/076* (2013.01); *A61B 5/686* (2013.01); *A61F 2/38* (2013.01);
(Continued)

(58) Field of Classification Search
CPC ......... A61B 5/076; A61B 5/686; A61B 90/98; A61F 2002/3067; A61F 2002/3071;
(Continued)

(56) References Cited

U.S. PATENT DOCUMENTS

2006/0082470 A1* 4/2006 Zhu ...................... G07B 15/063
340/928
2006/0111051 A1* 5/2006 Barink ................. G06K 7/0008
455/70

(Continued)

*Primary Examiner* — Dionne H Pendleton
(74) *Attorney, Agent, or Firm* — Eckert Seamans Cherin & Mellott, LLC; Philip E. Levy (57) ABSTRACT

A method of providing RF energy to a wireless transponder device includes outputting primary RF energy in a form wherein the primary RF energy comprises a plurality of RF bursts, with each consecutive pair of the RF bursts being separated by an associated time interval, and outputting secondary continuous wave RF energy in between each of the RF bursts of the primary RF energy during at least a portion of each of the associated time intervals. Also, a reader device implementing this method.

16 Claims, 4 Drawing Sheets

(51) Int. Cl.
*G01S 3/02* (2006.01)
*H04B 7/06* (2006.01)
*G01F 23/296* (2006.01)
*A61F 2/38* (2006.01)
*A61B 5/07* (2006.01)
*A61F 2/30* (2006.01)

(52) U.S. Cl.
CPC ............ *G01F 23/2962* (2013.01); *G01S 3/02* (2013.01); *H04B 7/0615* (2013.01); *H04B 7/0686* (2013.01); *H04B 7/0689* (2013.01); *A61F 2002/3067* (2013.01); *A61F 2002/3071* (2013.01)

(58) Field of Classification Search
CPC ............... A61F 2/38; B60R 16/037; B60W 2040/0809; B60W 40/08; G06F 17/3053; G06K 9/00362; G06K 9/00369; H04L 63/0861; H04L 63/102; G01F 23/2962; G01S 3/02; G01S 3/16; H04B 7/0615; H04B 7/0686; H04B 7/0689
See application file for complete search history.

(56) References Cited

U.S. PATENT DOCUMENTS

| | | |
|---|---|---|
| 2006/0232275 A1* | 10/2006 | Leussler ............ G01R 33/3692 324/322 |
| 2007/0173214 A1 | 7/2007 | Mickle |
| 2008/0129545 A1 | 6/2008 | Johnson et al. |
| 2008/0169928 A1 | 7/2008 | Mickle et al. |
| 2008/0183247 A1* | 7/2008 | Harding ............... A61N 1/0563 607/60 |
| 2009/0243837 A1 | 10/2009 | Chul Lee et al. |
| 2010/0013598 A1* | 1/2010 | Greene ................ G06K 7/0008 340/10.1 |
| 2010/0148965 A1 | 6/2010 | Alexis et al. |
| 2011/0187600 A1* | 8/2011 | Landt ....................... G01S 3/02 342/458 |

* cited by examiner

POWERING AND READING IMPLANTED DEVICES

CROSS-REFERENCE TO RELATED APPLICATIONS

This application claims priority under 35 U.S.C. § 119(e) from U.S. provisional patent application Ser. No. 61/823,598, entitled "Powering And Reading Implanted Devices" and filed on May 15, 2013, the contents of which are incorporated herein by reference.

BACKGROUND OF THE INVENTION

1. Field of the Invention

The present invention pertains to medical implant devices, such as, without limitation, orthopedic implants, cardiac implants, dental implants, general surgical implants, neurological implants, gastrointestinal implants, urological implants, gynecological implants, or some other implantable medical device, and, in particular, to a method and apparatus for powering such a medical implant device that includes a wireless transponder and/or for reading such a medical implant device having an associated sensor.

2. Description of the Related Art

U.S. Pat. Nos. 7,333,013 and 7,932,825 describe a system wherein a medical implant device, such as, without limitation, an orthopedic (e.g., an artificial knee or hip) or cardiac implant (e.g., a pacemaker), has a radio frequency identification (RFID) tag mounted thereto. The RFID tag stores information relating to the implant and/or the patient, such as, without limitation, the implant type/model/serial number, the implant manufacturer, the procedure date, the hospital and/or the implanting surgeon. That information may later be obtained from outside of the patient's body when needed by reading the RFID tag using a properly equipped RFID reader device. For example, that information can be read by the surgeon or another healthcare professional during a post operative or later visit in order to obtain information needed by that individual during the visit in order to properly examine and treat the patient. As another example, that information can also be read and transmitted to a secure patient database for use in medical outcomes research performed by, for example, a healthcare organization or implant manufacturer.

In one particular implementation, described in U.S. Pat. Nos. 7,333,013 and 7,932,825, the RFID tag mounted to the implant is a passive RFID tag that includes an antenna, and may be read using a conventional RFID reader that is structured to read the implanted passive RFID tag over an air interface. In another particular implementation, an alternative RFID reader may be used, wherein the RFID reader is structured and configured to read the implanted RFID tag by making a direct (i.e., non-air interface) electrical connection to the RFID tag through the patient's living tissue using a probe provided as part of the RFID reader device (e.g., using transcutaneous contact and transcutaneous near field communication (TNFC) or transcutaneous for field communication (TFFC)). This latter implementation is described in U.S. Pat. Nos. 6,487,844, 7,228,183 and 7,825,807. In both of these implementations, the implanted RFID tag is powered by harvesting energy from the RF energy provided by the RFID reader.

Certain passive RFID tags provide a voltage output connection for powering other devices when such power is available from the energy harvested from an RFID reader. One use of this voltage is to power implanted sensors, which may be very simple in design because the RFID system provides a convenient method to communicate with the associated electronics.

Figure 1:
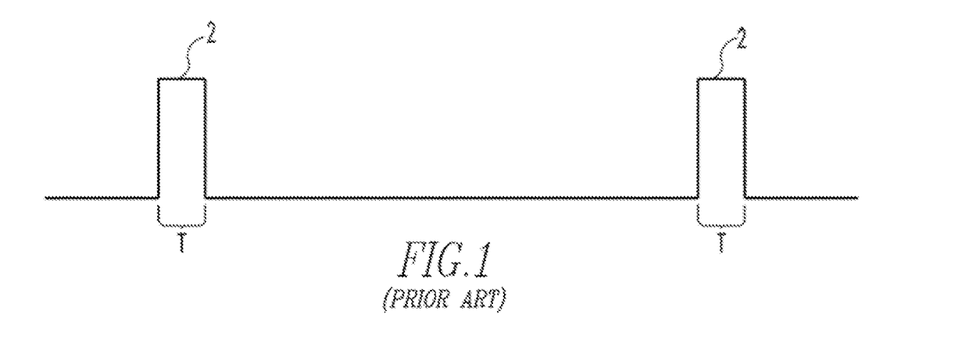
FIG. 1 is a schematic representation of the RF output of a prior art RFID reader device.

As is known in the art, and as shown in FIG. 1, prior art RFID readers power and communicate with a passive RFID tags through relatively short bursts 2 of radio frequency (RF) energy (also known as RF pulses having a square wave format). The duration of these bursts 2 is limited by the FCC.

Figure 2:
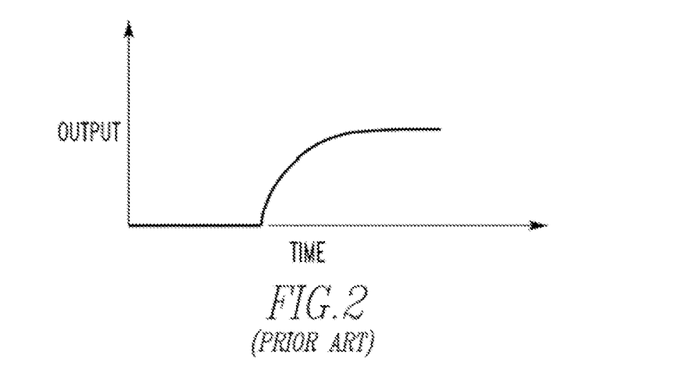
FIGS. 2 and 3 are schematic representations of the output of prior art sensors showing RC and RL dynamics, respectively.
Figure 3:
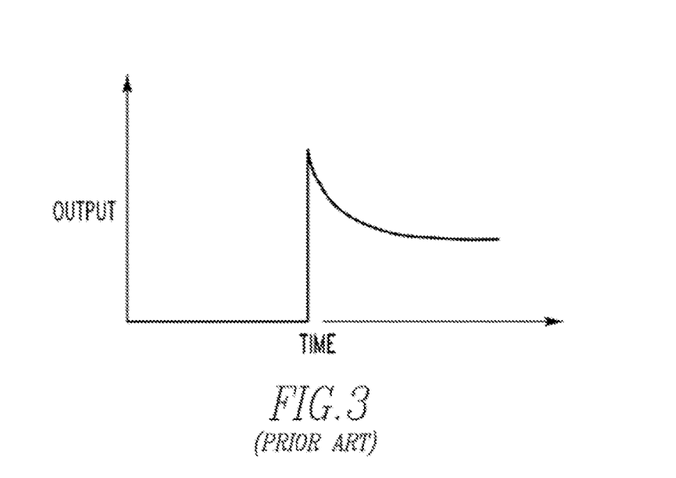

One type of sensor often used in association with passive RFID tags changes its conductivity when connected in an electrical circuit in order to report variations in the parameter to be measured. In one such embodiment, the sensor device is a voltage divider and is typically categorized as a resistor, i.e., a variable resistor. While an ideal variable resistor will essentially have an instantaneous response to an RF burst, such as burst 2, from an RFID reader, actual sensor implementations have dynamics associated with them where it takes a nonzero time for the sensor to reach a steady state output value. This behavior is similar to that of a resistive/capacitive (RC) circuit, exhibiting what is termed an RC time constant (shown in FIG. 2), or, alternatively, a resistive/inductive (RL) circuit, exhibiting what is termed an RL time constant (shown in FIG. 3), or some combination of both RC and RL dynamics.

If the RC and/or RL dynamics of the sensor are sufficiently fast, the reading can be accomplished within the time duration) of the energy burst of the RFID reader (e.g., within the duration, T, of burst 2 shown in FIG. 1). However, if the RC and/or RL dynamics of the sensor are such that the sensor is not able to reach an accurate steady state value within the duration of the energy burst of the RFID reader (e.g., within the duration, T, of burst 2 shown in FIG. 1), then problems will arise. In such a case, in order to get an accurate reading, the time during which RF energy used for powering is provided must be extended. However, FCC regulations limit the duration of RF bursts that may be output by an RFID reader or similar device over an air medium (i.e., the regulations set a maximum length for such duration). Thus, due to the FCC regulations, manufacturers of commercial off the shelf (COTS) RFID reader devices will not be willing to alter their devices to allow them to exceed this regulated limit because COTS RFID reader devices are specifically designed to transmit over an air medium. Furthermore, while the application of the reader in the transcutaneous method described above is not an over the air regulated situation, asking the COTS reader manufacturers to alter their reader would defeat the COTS availability of such readers for a much wider market.

SUMMARY OF THE INVENTION

In one embodiment, an RFID reader device is provided that includes a primary RF source structured to output primary RF energy in a form wherein the primary RF energy comprises a plurality of RF bursts, with each consecutive pair of the RF bursts being separated by an associated time interval, and a supplemental RF source structured to output secondary continuous wave RF energy in between each of the RF bursts of the primary RF energy during at least a portion of each of the associated time intervals.

In another embodiment, a method of providing RF energy to a wireless transponder device is provided. The method includes outputting primary RF energy in a form wherein the primary RF energy comprises a plurality of RF bursts, with each consecutive pair of the RF bursts being separated by an associated time interval, and outputting secondary continuous wave RF energy in between each of the RF bursts of the primary RF energy during at least a portion of each of the associated time intervals.

In still a further embodiment, a wireless transponder device is provided that includes electronic circuitry structured to receive an output of a sensor device associated with the wireless transponder device, the output having a transient response portion followed by a steady state portion, and determine a reading for the sensor device based on the transient response portion and not the steady state portion of the output.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 4:
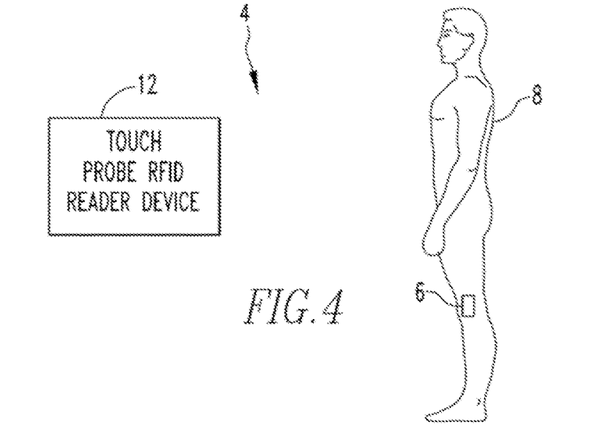
FIG. 4 is a schematic diagram of an RFID system according to an exemplary embodiment of the present invention wherein information may be read from and written to a medical implant that has been surgically implanted in a patient.
Figure 5:
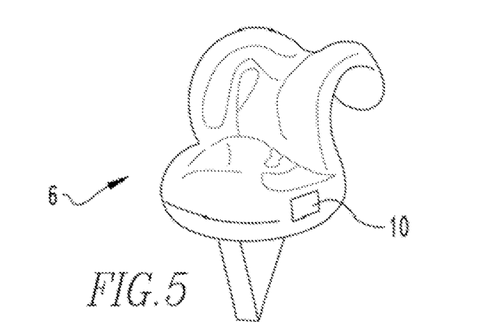
FIG. 5 is an isometric, view of an exemplary medical implant that may be used in the system of FIG. 4.

FIG. 4 is a schematic diagram of an RFID system 4 according to an exemplary embodiment of the present invention wherein information may be read from and written to a medical implant 6 (such as, without limitation, an artificial knee shown schematically in the illustrated embodiment and in an isometric view in FIG. 5) that has been surgically implanted in a patient 8. As described in greater detail herein, medical implant 6 has a passive RFID transponder device 10 (e.g., a passive RFID tag) (FIG. 5) coupled thereto that may be read using touch probe RFID reader device 12 (described in greater detail elsewhere herein) that is structured and configured to read the implanted RFID transponder device 10 by making a direct (i.e., non-air interface) electrical connection to RFID transponder device 10 through the living tissue of patient 8 using a probe provided as part of touch probe RFID reader device 12 (e.g., using transcutaneous contact and transcutaneous near field communication (TNFC) or transcutaneous far field communication (TFFC)).

As described above, RFID transponder device 10 is a passive device powered by the RF signal sent by touch probe RFID reader device 12. One passive tag technology, known as backscatter technology, generates signals by backscattering the carder signal sent from the RFID reader. In another technology, described in U.S. Pat. Nos. 6,289,237, 6,615, 074, 6,856,291, 7,057,514, and 7,084,605 (and commonly referred to as energy harvesting), RF energy from the RFID reader is harvested and converted to a DC voltage by an antenna/matching circuit/charge pump combination. The DC voltage is then used to power the circuitry that transmits information to the RFID reader at, for example, a different frequency.

Figure 6:
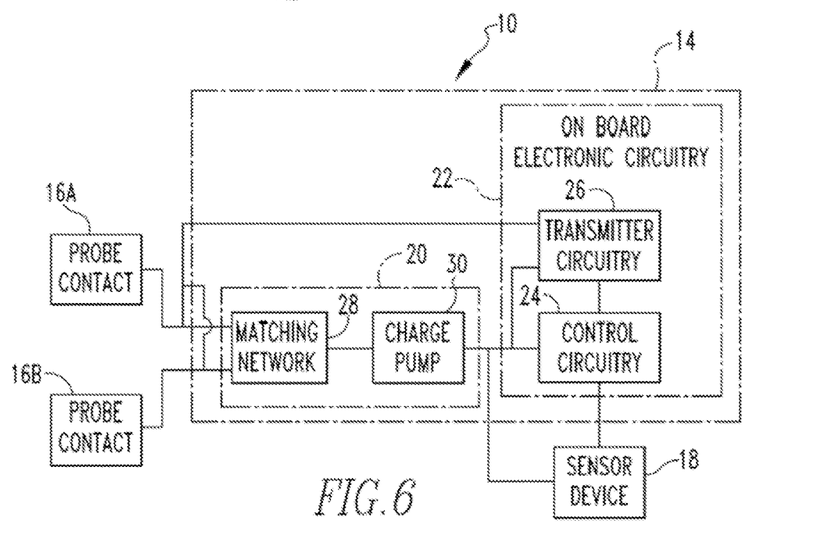
FIG. 6 is a schematic representation of one particular, non-limiting embodiment of a passive RFID transponder device that may be employed in the system of FIG. 4.

FIG. 6 is a schematic representation of RFID transponder device 10 according to one particular, non-limiting embodiment of the present invention wherein passive technology in the form of energy harvesting as just described is employed to power the electronic components of RFID transponder device 10. RFID transponder device 10 includes an integrated circuit chip 14 operatively coupled to probe contacts 16A and 16B in the form of interfacing conductors, the function of which is described herein.

In addition, RFID transponder device 10 further includes an implanted sensor device 18 that is operatively coupled to integrated circuit chip 14. Sensor device 18 is structured to measure one or more parameters relating to the state (e.g., health state) of patient 8 and provide that information to integrated circuit chip 14 so that it may then be communicated to touch probe RFID reader device 12 as described herein. In the exemplary embodiment, sensor device 18 exhibits RC and/or RL dynamics such that it take a certain time period for sensor device 18 to reach an accurate steady state value when it is making a measurement. Thus, in the exemplary embodiment, the output of sensor device 18 will resemble one of FIGS. 2 and 3 (depending on the particular configuration of sensor device 18).

As seen in FIG. 6, integrated circuit chip 14 of the present embodiment also includes energy harvesting circuitry 20 that is operatively coupled to (i) probe contacts 16A and 16B at an input end thereof, and (i) on-board electronic circuitry 22 and sensor device 18 at an output end thereof. In the illustrated embodiment, on-board electronic circuitry 22 includes control circuitry 24, such as a microprocessor, a microcontroller or some other suitable custom control circuitry along with an associated memory, and transmitter circuitry 26. In operation, energy harvesting circuitry 20 is structured to receive RF energy from RFID reader device 12 (via a touch probe in the manner described herein) and harvest energy therefrom by converting the received RF energy into DC energy, e.g., a DC voltage. The DC voltage is then used to power on-board electronic circuitry 22 and sensor device 18. Transmitter circuitry 26 is structured to transmit an RF information signal to RFID reader device 12 through probe contacts 16A and 16B.

In the particular embodiment shown in FIG. 6, energy harvesting circuitry 20 of integrated circuit chip 14 includes a matching network 28 electrically connected to probe contacts 16A and 16B. Matching network 28 is also electrically connected to a voltage boosting and rectifying circuit preferably in the form of a one or more stage charge pump 30. Charge pumps are well known in the art. Basically, one stage of a charge pump increases the effective amplitude of an AC input voltage with the resulting increased DC voltage appearing on an output capacitor. Successive stages of a charge pump, if present, will essentially increase the voltage from the previous stage resulting in an increased output voltage. In operation, probe contacts 16A and 16B receive RF energy that is provided by RFID reader device 12 as described herein. The received RF energy is provided, in the form of an AC signal, to charge pump 30 through the associated matching, network 28. Charge pump 30 rectifies the received AC signal to produce a DC signal that is amplified as compared to what it would have been had a simple rectifier been used. In the exemplary embodiment, matching network 28 is chosen (i.e., its impedance is chosen) so as to maximize some criterion such as the voltage of the DC signal output by charge pump 30.

Figure 7:
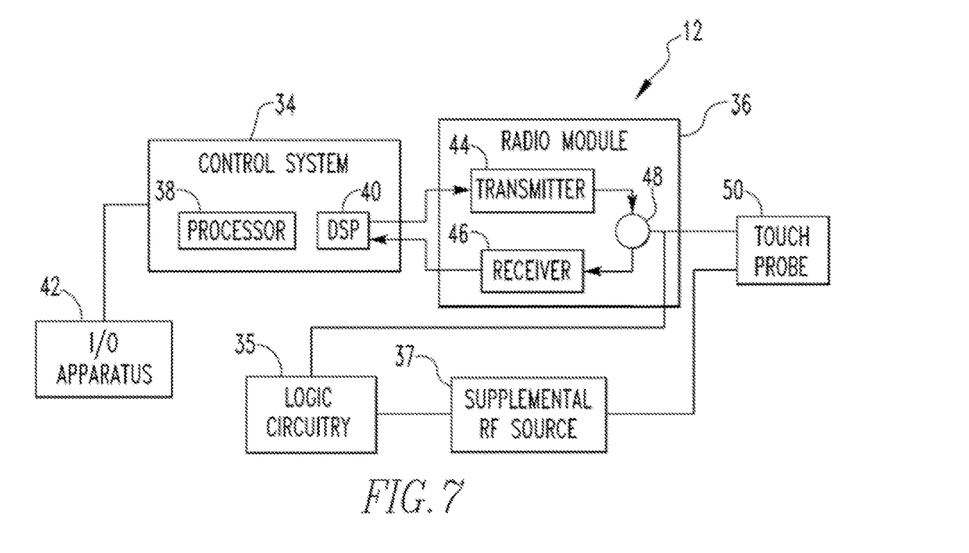
FIG. 7 is a schematic diagram of a touch probe RFID reader device according to one non-limiting exemplary embodiment that may be employed in the system of FIG. 4.

FIG. 7 is a schematic diagram of touch probe RFD reader device 12 according to one non-limiting exemplary embodiment of the present invention. As noted elsewhere herein and as described in detail below, touch probe RFID reader device 12 is able to read information from and write information to RFID transponder device 10 by making a direct (i.e., non-air interface) electrical connection thereto. RFID reader device 12 includes a control system 34, a primary radio module 36, logic circuitry 35, and a supplemental RF source 37, such as, without limitation, an RF oscillator.

In the exemplary embodiment shown in FIG. 7, control system 34 includes a processor 38, such as a microcontroller or microprocessor, and a digital signal processor (DSP) 40, although other configurations are possible. Processor 38 provides control over high level operation of touch probe RFID reader device 12 and may communicate with an external network and/or peripheral devices such as, without limitation, an I/O apparatus 42 (which enables information to be input into and output from touch probe RFID reader device 12). I/O apparatus 42 may include a display, a keyboard, a touchscreen, or some combination thereof. DSP 40 provides direct control over all operations of radio module 36 in response to high level commands provided by processor 38, and processes data signals received from RFID transponder device 10 as described herein. Radio module 36 is adapted to provide for communications to/from RFID transponder device 10 by generating and receiving. RF signals in the manner described herein, and is structured to provide an RF output that resembles the output shown in FIG. 1 (i.e., a number of RF bursts 2 each having a duration as governed/limited by FCC regulations).

More particularly, radio module 36 further comprises a transmitter portion 44, a receiver portion 46, and a hybrid 48. Hybrid 48 may further comprise a circulator. Transmitter portion 44 preferably includes a local oscillator that generates an RF carrier frequency. Transmitter portion 44 sends a transmission signal modulated by the RF carrier frequency to hybrid 48, which in turn passes the signal to a touch probe device 50. Hybrid 48 connects transmitter portion 44 and receiver portion 46 to touch probe device 50 while isolating them from each other. In particular, hybrid 48 allows a relatively strong signal to be sent from transmitter portion 44 while simultaneously receiving a weaker signal received from RFID transponder device 10. Touch probe device 50 includes one or more electrical contacts or electrodes that are adapted to be selectively and temporarily mated and brought into electrical contact with probe contacts 16A and 16B of RFID transponder device 10. As such, the signals generated by touch probe RFID reader device 12, that would in known RFID readers be sent over an air interface, ma instead be directly transmitted (i.e., not over an air interface) to RFID transponder device 10 (e.g., through the living tissue of patient 8), and thus integrated circuit chip 14 provided therein. Similarly, the signals generated by integrated circuit chip 14, that in the prior art would have been sent via antenna over an air interface to an RFID reader, may instead be directly transmitted (i.e., not over an air interface) to RFID reader device 12 through touch probe device 50, in one particular embodiment, touch probe device 50 is a wand-like device having two conductors fixed at the end thereof with a center to center distance to accommodate the spacing of probe contacts 16A and 16B. In this embodiment, the wand-like touch probe device 50 is used to manually bring the conductors into electrical contact with probe contacts 16A and 16B through the tissue of patient 8 (i.e., transcutaneous contact) as needed.

The signals from RFID transponder device 10 (which may, for example, include the readings of sensor device 18) transmitted through touch probe device 50 are passed back to hybrid 48, which forwards the signals to receiver portion 46. Receiver portion 46 mixes the captured signals with the RF carrier frequency generated by the local oscillator to directly downconvert the captured signals to a baseband information signal, which is provided to DSP 40 for processing thereby.

In the exemplary embodiment, the RC and/or RL dynamics of sensor device 18 are such that it is not able to reach an accurate steady state value within the duration of the RF energy bursts output by touch probe RFID reader device 12. Thus, in order to avoid problems in obtaining accurate readings from sensor device 18, touch probe RFID reader device 12 is, as described, below, structured in a manner to provide RF energy used for powering for an extended period.

More specifically, as seen in FIG. 7, touch probe RFID reader device 12 also includes logic circuitry 35 and supplemental RF source 37 which together are structured to provide RF energy that may be used for powering RFID transponder device 10 during the periods in between the RF energy bursts output by touch probe RFID reader device 12. In operation, logic circuitry 35 monitors the output of radio module 36 to detect the end (falling edge) of each RF burst output by radio module 36. In response to detecting the end of an RF burst, logic circuitry 35 sends a trigger signal to supplemental RF source 37 which causes supplemental RF source 37 to output a second RF continuous wave (CW) to touch probe 50 for a certain time period/duration such that RF continuous wave output will end just before radio module 36 produces its next RF burst (the certain time period/duration of the secondary RF CW may be programmed based on the known interval between the RF bursts of radio module 36). The secondary RF CW output by does not need to be modulated.

Figure 8:
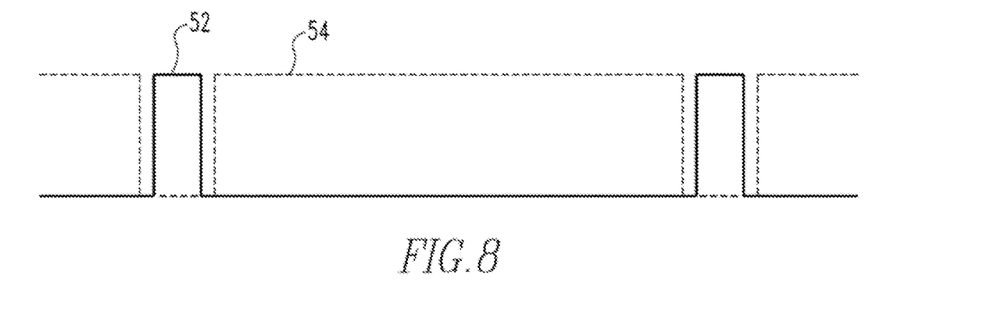
FIG. 8 is a schematic representation of the output of the touch probe RFID reader device of FIG. 7.

Thus, the combined output to touch probe 50 will appear as shown in FIG. 8, wherein waveform 52 (solid line) represents the output of radio module 36 and waveform 54 (dotted line) represents the output of supplemental RF source 37. As will be appreciated, the addition of the secondary RF CW from supplemental RF source 37 will provide extended powering time for sensor device 18 to reach a steady state value. As seen in FIG. 8, there can be short intervals with no RF energy supply during the period that radio module 36 is shutting off its burst, and supplemental RF source 37 is turning on, and during the period when supplemental RF source 37 is shutting down and radio module 36 is turning on. This is not a problem in that if sensor device 18 has dynamics requiring additional time for charging, those same dynamics win allow for short intervals of no RF energy.

Furthermore, while RFID transponder device 10 shown in FIG. 6 is one exemplary embodiment of a passive RFID transponder that may be used in connection with the concepts of the present invention, it will be understood that that is not meant to be limiting and that alternative passive RFID transponder implementations may also be used. For example, and without limitation, alternative passive RFID transponder implementations may be as shown and described in U.S. patent application Ser. No. 13/552,225, the disclosure of which is incorporated herein by reference, including the implementations that employ an RFID strap.

In addition, in the exemplary embodiment, touch probe RFID reader device 12 employs a touch probe 50 having two electrical contacts. It will be understood, however, that the concept of the present invention may also be employed in a touch probe RFID reader device having a single electrical contact (a mono-probe) in conjunction with appropriately configured passive RFID transponder implementations as described in U.S. patent application Ser. No. 13/552,225.

Moreover, in one embodiment, the reading of sensor device 18 is based on the steady state output value of sensor device 18. In some implementations, however, the steady state output values of sensor device 18 may vary by only small amounts, thus making it difficult to discern different sensor readings. Thus, according to an alternative embodiment, the reading of sensor device 18 is based not on the steady state signal of sensor device 18, but instead on the transient portion of the signal that is output by sensor device 18.

Figure 9:
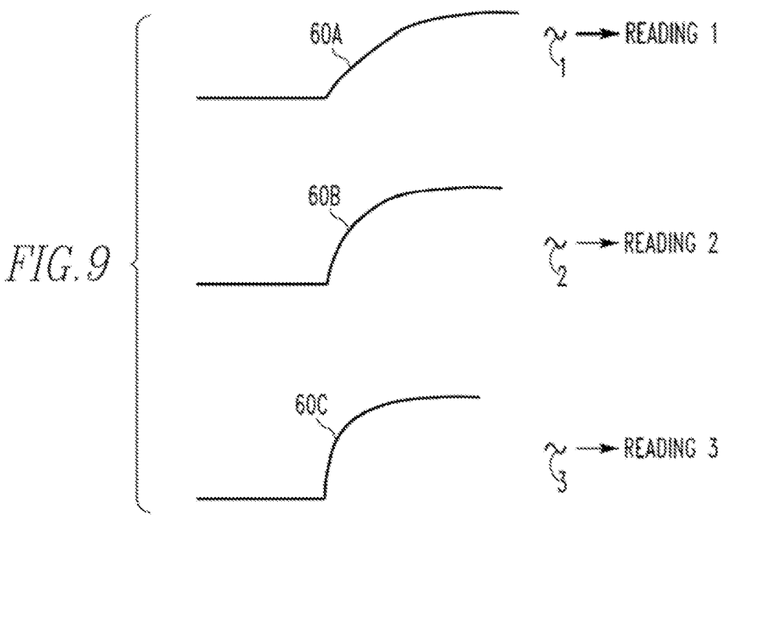
FIGS. 9 and 10 are schematic representations showing how the transient outputs of is sensor device can be correlated to sensor reading in one particular exemplary embodiment.
Figure 10:
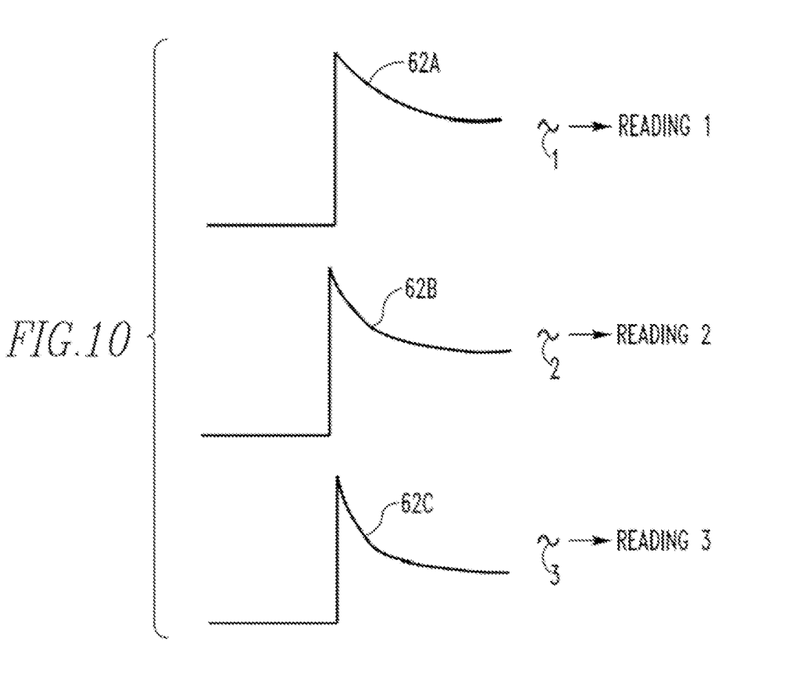

More specifically, as noted elsewhere herein, sensor device 18 exhibits RC and/or RL dynamics such that its output for any particular reading will have a transient response portion followed by a steady state portion. The transient response portion will resemble an RC or RL curve as shown in, for example, FIGS. 2 and 3, and may be characterized as a first order linear time invariant (LTI) system. As is known in the art, each such transient response portion will be characterized by and have associated with it a time constant which indicates how fast the transient output reaches a steady state value, and more particularly is the time that it takes the transient output to reach a certain % (about 63.2%) of either its initial value or its steady state value. In the present alternative embodiment, each one of a family of possible transient outputs of sensor device 18 is correlated to a particular sensor reading/value so that the sensor reading/value of sensor device 18 is able to be based on some characteristic, such as the time constant, of the transient response portion of the output of sensor device 18 (rather than the steady state portion). This is illustrated in one embodiment in FIG. 9, wherein a plurality of different possible transient outputs (labeled 60A, 60B, 60C) of sensor device 18 (each having an RC curve form) are shown, with each one having an associated time constant ($\tau$) that is correlated to a particular sensor reading/value, and in another embodiment in FIG. 10, wherein another plurality of different possible transient outputs (labeled 62A, 62B, 62C) of sensor device 18 (each having an RL curve form) are shown, with each one having an associated time constant ($\tau$) that is correlated to a particular sensor reading/value.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere filet that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A radio frequency identification reader device, comprising:
   a primary radio frequency source structured to output primary radio frequency energy in a form wherein the primary radio frequency energy comprises a plurality of radio frequency bursts, each consecutive pair of the radio frequency bursts being separated by an associated time interval;
   a supplemental radio frequency source structured to output secondary continuous wave radio frequency energy in between each of the radio frequency bursts of the primary radio frequency energy during at least a portion of each of the associated time intervals; and
   control circuitry structured to detect an end of each of the radio frequency bursts and responsive to each detection cause the supplemental radio frequency source to output the secondary continuous wave radio frequency energy during at least a part of the time interval associated with the radio frequency burst.

2. The radio frequency identification reader device according to claim 1, further comprising a touch probe coupled to the primary radio frequency source and the supplemental radio frequency source, the touch probe being structured to receive the primary radio frequency energy and the secondary continuous wave radio frequency energy and to provide the primary radio frequency energy and the secondary continuous wave radio frequency energy to a wireless transponder device through a direct electrical connection not over an air interface between the touch probe and the wireless transponder device.

3. The radio frequency identification reader device according to claim 2, wherein the direct electrical connection is through transcutaneous contact.

4. The radio frequency identification reader device according to claim 1, wherein the supplemental radio frequency source comprises an radio frequency oscillator.

5. The radio frequency identification reader device according to claim 4, wherein the primary radio frequency source is part of a commercial off the shelf radio frequency identification reader device and the supplemental radio frequency source and the control circuitry are separate from the commercial off the shelf radio frequency identification reader device.

6. A method of providing radio frequency energy to a wireless transponder device, comprising:
outputting primary radio frequency energy in a form wherein the primary radio frequency energy comprises a plurality of radio frequency bursts, each consecutive pair of the radio frequency bursts being separated by an associated time interval;
outputting secondary continuous wave radio frequency energy in between each of the radio frequency bursts of the primary radio frequency energy during at least a portion of each of the associated time intervals; and
detecting an end of each of the radio frequency bursts and responsive to each detection causing the secondary continuous wave radio frequency energy to be output during at least a part of the time interval associated with the radio frequency burst.

7. The method according to claim 6, further comprising receiving the primary radio frequency energy and the secondary continuous wave radio frequency energy in a touch probe and providing the primary radio frequency energy and the secondary continuous wave radio frequency energy to the wireless transponder device through a direct electrical connection not over an air interface between the touch probe and the wireless transponder device.

8. The method according to claim 7, wherein the direct electrical connection is through transcutaneous contact.

9. A method of reading a sensor device associated with a wireless transponder device structured and configured to be read by a radio frequency identification reader device, comprising:
receiving in the wireless transponder device an output of the sensor device, the output having a transient response portion followed by a steady state portion; and
determining in the wireless transponder device a reading for the sensor device based on the transient response portion and not the steady state portion of the output, wherein the wireless transponder device is structured and configured to communicate the determined reading for the sensor device to the radio frequency identification reader device.

10. The method according to claim 9, wherein the determining is based on a characteristic of the transient response portion.

11. The method according to claim 10, wherein the characteristic is a time constant of the transient response portion.

12. The method according to claim 9, wherein the sensor device exhibits resistive/capacitive dynamics, resistive/inductive dynamics, or a combination of resistive/capacitive dynamics and resistive/inductive dynamics.

13. A wireless transponder device structured and configured to be read by a radio frequency identification reader device, comprising:
electronic circuitry structured to: (i) receive an output of a sensor device associated with the wireless transponder device, the output having a transient response portion followed by a steady state portion, and (ii) determine a reading for the sensor device based on the transient response portion and not the steady state portion of the output, wherein the wireless transponder device is structured and configured to communicate the determined reading for the sensor device to the radio frequency identification reader device.

14. The wireless transponder device according to claim 13, wherein the electronic circuitry is structured to determine the reading based on a characteristic of the transient response portion.

15. The wireless transponder device according to claim 14, wherein the characteristic is a time constant of the transient response portion.

16. The wireless transponder device according to claim 13, wherein the sensor device exhibits resistive/capacitive dynamics, resistive/inductive dynamics, or a combination of resistive/capacitive dynamics and resistive/inductive dynamics.

* * * * *